United States Patent
Figge (10) Patent No.: US 7,562,578 B2
(45) Date of Patent: Jul. 21, 2009

(54) METHOD AND APPARATUS FOR DETECTING SURFACE DEFECTS IN ROLLING MILL ROLLERS

(75) Inventor: Dieter Figge, Essen (DE)

(73) Assignee: SMS Demag AG, Düsseldorf (DE)

( * ) Notice: Subject to any disclaimer, the term of this patent is extended or adjusted under 35 U.S.C. 154(b) by 208 days.

(21) Appl. No.: 11/597,862

(22) PCT Filed: Oct. 19, 2005

(86) PCT No.: PCT/EP2005/011225

§ 371 (c)(1),
(2), (4) Date: Nov. 28, 2006

(87) PCT Pub. No.: WO2006/042748

PCT Pub. Date: Apr. 27, 2006

(65) Prior Publication Data
US 2008/0028859 A1    Feb. 7, 2008

(30) Foreign Application Priority Data
Oct. 20, 2004  (DE) .................. 10 2004 051 020

(51) Int. Cl.
*G01N 29/27* (2006.01)
(52) U.S. Cl. .......................... 73/639; 73/618
(58) Field of Classification Search .................. 73/618, 73/635, 639, 637
See application file for complete search history.

(56) References Cited

U.S. PATENT DOCUMENTS 3,745,815 A * 7/1973 Uozumi ..................... 73/639
3,868,847 A    3/1975 Gunkel et al.
4,423,636 A    1/1984 Plante et al.
5,417,114 A    5/1995 Wadaka et al.
5,469,743 A * 11/1995 Zorn ........................... 73/627
6,105,431 A    8/2000 Duffill et al.
6,341,525 B1   1/2002 Takada et al.

FOREIGN PATENT DOCUMENTS

GB        1 561 811        3/1980

OTHER PUBLICATIONS

Komsky: "Rolling Dry-Coupled Transducers for Ultrasonic Inspections . . . of aging aircraft structures" in Health Monitoring and Smart Nondestructive Evaluation of Structural and Biological Systems III, Mar. 15-17, 2004, San Diego, Calif., USA, vol. 5, 394, No. 1, pp. 201-209.

* cited by examiner

*Primary Examiner*—John E Chapman
(74) *Attorney, Agent, or Firm*—Friedrich Kueffner (57) ABSTRACT

The invention relates to a method, device and a circuit for detecting surface defects such as cracks, fractures and the like on a roller (2) for a rolling mill (1), in particular on the working rollers (2a) which are mounted with support roller (2b) on a vertical stand (3). The rollers (2) are verified for detecting defects in the operation position thereof, transversal ultrasonic waves (4a) whose frequency is approximately equal to 0.5-2 MHz are transmitted to the first end of the roller (2c) and are received on the second end (2d) thereof and during a measuring process an ultrasound transducer (5) and an ultrasound receiver (6) are pressed against the cylinder (2e) surface for a test time.

12 Claims, 9 Drawing Sheets

METHOD AND APPARATUS FOR DETECTING SURFACE DEFECTS IN ROLLING MILL ROLLERS

The invention concerns a method and a device for determining surface defects such as cracks, spalling, and the like, on rolling mill rolls, especially work rolls that are supported with backup rolls in housing posts, by the use of ultrasonic waves.

In the rolling mill sector, it is customary to change the work rolls in hot strip mills and cold rolling mills after a predetermined period of use, which depends on the rolling mill material and other rolling parameters. However, the resulting time factor cannot take serious defects in the given roll into account. For want of additional precise diagnosis, the work rolls are often changed much too early. This results in economic disadvantages.

DE 198 49 102 C1 discloses a method and a device for the nondestructive testing of objects for defects in the structure at and/or near the surface by means of Rayleigh waves. The angles of incidence ($\alpha$) are set at $1.04\pm0.2°$ of the angle obtained from the quotient of the speed of sound in the medium in front of the surface and the speed of the Rayleigh wave in the article or test object.

However, the application of this method to rolling stand rolls is already out of the question due to the nature of the underlying principles of the method and the proposed device.

U.S. Pat. No. 4,423,636 discloses a test method in which ultrasound is introduced by a sound wave transducer into a roll to be tested and is then received at a different point by a receiver. Plate-shaped elements are brought into contact with the surface of the roll to transmit and receive the sound.

The basic possibility of carrying out nondestructive testing by ultrasonic waves is disclosed in U.S. Pat. No. 6,105,431. The sound waves are introduced into the test material at an angle and are detected again at a point distant from the ultrasonic transducer.

Similar solutions are known from U.S. Pat. No. 6,341,525, GB 1,561,811 A, U.S. Pat. Nos. 5,417,114, 3,868,847, and from the paper by I. Komsky entitled "Rolling dry-coupled transducers for ultrasonic inspections of aging aircraft structures" in Health Monitoring and Smart Nondestructive Evaluation of Structural and Biological Systems III, Mar. 15-17, 2004 San Diego, Calif., USA, Vol. 5,394, No. 1, p. 17.

The objective of the invention is to make it possible to apply the ultrasonic test method, which in itself is already well known, to elongated parts of rolling mills in their operating position, namely, to wear-endangered rolls, and to simplify this method.

In accordance with the invention, this objective is achieved by testing the roll in which defects are to be detected in its installed position, wherein generated ultrasonic transverse waves (so-called shear waves) with a frequency of about 0.5 to 2 MHz are introduced at one end of the roll and received at the other end of the roll, and wherein during the measuring operation, an ultrasonic transducer and an ultrasonic receiver are pressed against the surface of the roll for the duration of the test. The speed of sound is about 50% lower in transverse waves than in longitudinal waves. This reduced speed of sound is also associated with a reduced wavelength, so that even very small cracks can be detected. Defects in the surface of the rolls are defined here as cracks and checks and spalling with dimensions of 0.6×0.6 mm. The cracks are assumed to have a width of 50 µm and a depth of 10 µm. The frequency of 0.5 to 2 MHz represents a compromise between a maximum measuring depth and a standard resolution for detecting even small defects. The arrangement of the ultrasonic transducer at one end of the roll and the ultrasonic receiver at the other end of the roll requires the least power consumption. Changes in acoustic properties occur at the boundaries of these defects, and these changes can be detected by various measuring techniques.

The roll materials that can be tested include especially the following:

Steel roll for cold rolling mills: The sound transmission coefficient of forged steel is especially high due to its fine-grained structure.

Rolls made of cast steel: The structure is slightly more coarse-grained compared to forged steel; however, the material can still be tested well when the testing frequency is reduced. Rolls of this type are used, for example, as high-chromium steel rolls for the first rolling stands of hot strip finishing trains.

Indefinite chill rolls: These rolls have a core that consists of spheroidal graphite iron and a jacket that consists of a chill casting. This type of roll is difficult to test due to the graphite inclusions that are present. This can lead to a high level of acoustic scattering. Ultrasound frequencies less than 1 MHz are suggested for the testing. This type of rolling mill roll is used as a composite cast roll for the last rolling stands of hot strip finishing train.

Backup rolls made of forged steel: The possibility of testing by ultrasound at frequencies around 1 MHz is very favorable.

In one embodiment, the ultrasonic transducer and the ultrasonic receiver are applied radially at the edge of the barrel, close to the roll neck, which is supported in the housing bearing.

In an improved embodiment, when the ultrasonic transducer and the ultrasonic receiver are being applied, the roll in which defects are to be detected is stopped, and then, after the transducer and receiver have been applied, the roll is turned by about two revolutions. After the testing process, the devices can be swung away again. The rolling stock guides and cooling devices that are present are not hindered by the these devices.

In a refinement, the ultrasonic waves are conveyed via a piezoelectric element through a core part of transparent plastic and an adjacent silicone filling to a roller-shaped contact body made of steel, which is pressed against the roll surface beyond the roll barrel. The piezoelectric element serves the purpose of bundling the family of waves and thus systematically guiding the ultrasonic waves in the predetermined direction.

To obtain conductive transmission of the incident ultrasonic waves, an iridium coating is applied on the outer running surface of the roller-shaped contact body.

In accordance with another advantageous measure, the testing operation is carried out without rolling stock between the work rolls. The testing operation can be carried out after a change of rolling stock or during a pause provided for this purpose.

In accordance with other steps, the ultrasonic waves are introduced into the surface of the roll at an acute angle, and only the component in the direction of the roll surface is utilized.

In accordance with the invention, the device for determining surface defects such as cracks, spalling, and the like, in rolling mill rolls, especially work rolls that are supported with backup rolls in housing posts, with the use of ultrasound, achieves the objective of the invention by virtue of the fact that a holder, which can be swiveled out of a parking position and into a testing position or vice versa, is supported in the housing posts, wherein the holder holds either an ultrasonic transducer or an ultrasonic receiver, and wherein the holders can each be adjusted to a definite contact force by means of a drive. This makes it possible not only to test different roll diameters according to their wear or dressing, but also always to maintain the contact force at a suitable level.

In accordance with a further refinement of the invention, a roller-shaped contact body made of steel is arranged at the pressing ends of the swivel arms. The contact angle with the surface of the roll varies only slightly with different roll diameters.

The contact body creates the condition for uniform transmission of ultrasonic waves to the steel roll and their further conduction from the transducer to the receiver. To this end, it is advantageous for the contact body to have a stationary core part made of plastic, which is rotationally rigidly connected with a head housing by a coupling (e.g., an Oldham coupling), wherein the core part is supported in the roller-shaped contact body in such a way that it can rotate smoothly, and wherein an electrically connected wave transducer or wave receiver is mounted in the contact body. In this way, the device creates bundled wave generation and further conduction within the roll.

In an improved modification, the outer surface of the roller-shaped contact body is coated with iridium. This increases the transmissivity of ultrasonic waves through the contact roller to the roll to be tested.

In conformity with the otherwise customary liquid coupling media, which cannot be provided on the mounted roll, it is proposed that the annular space between the roller contact body and the stationary plastic core part be filled with silicone for acoustic coupling.

In addition, an electric/electronic circuit is proposed for determining surface defects such as cracks, spalling, and the like, on rolling mill rolls, especially work rolls that are rotatably supported with backup rolls in housing posts, by the use of ultrasonic waves.

This circuit achieves the stated objective in such a way that an ultrasonic transducer is connected to an ultrasonic generator and, through the roll, with an ultrasonic receiver, which is connected to a receiver amplifier and a comparator; that a memory for sample measuring signals is connected with a parallel amplifier for the samples and with the comparator; and that a predetermined sample measuring signal is generated in an error signal generator connected to the comparator.

The circuit is expanded in such a way that the error signal generator is connected to a recorder with memory.

Furthermore, in another embodiment, it is provided that a relay to a following or preceding sample measuring signal is connected to the recorder for a detected sample measuring signal.

Specific embodiments of the invention are illustrated in the drawings and are explained in greater detail below.

Figure 1:
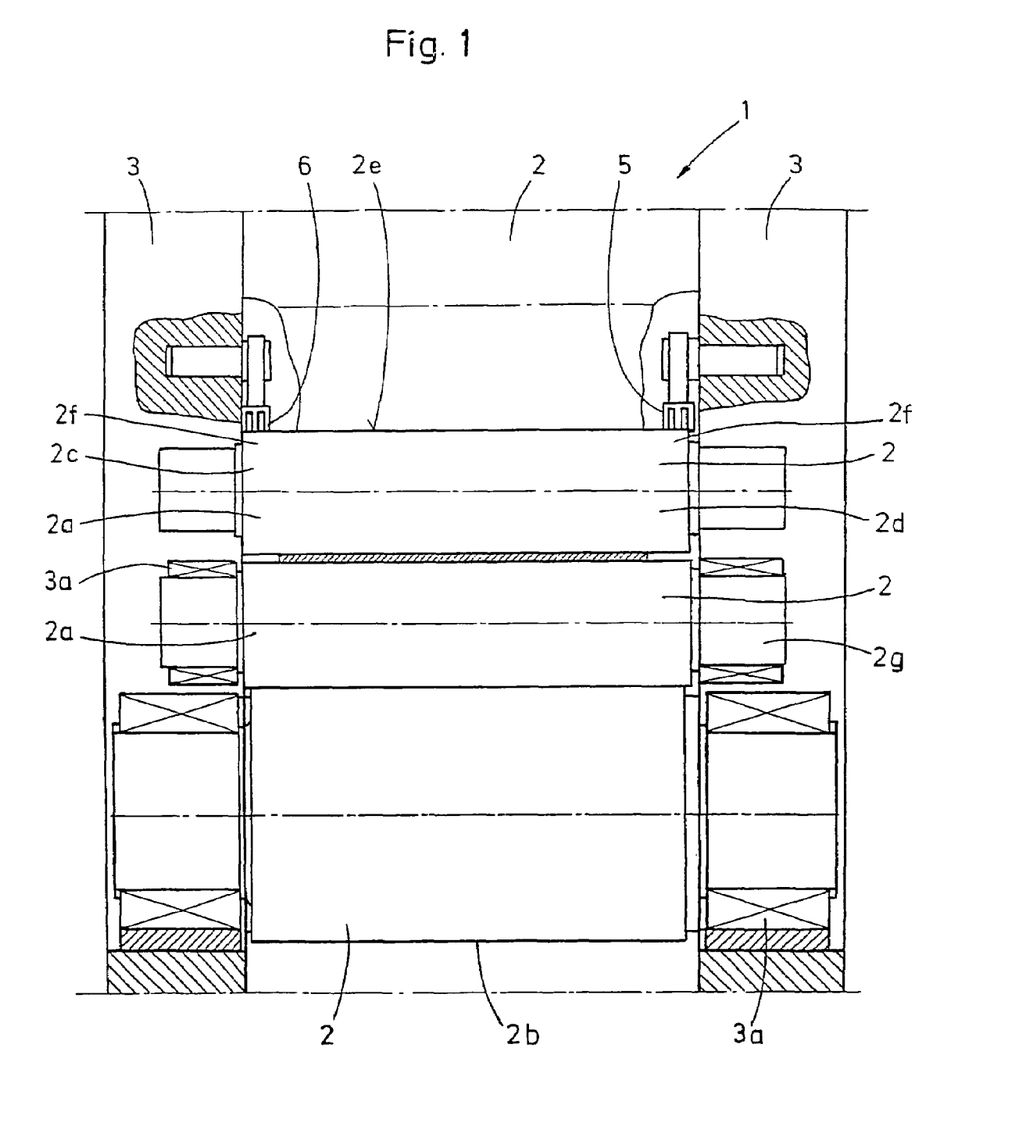
FIG. 1 shows a front elevation of a four-high rolling stand of a rolling mill in the rolling direction.

FIG. 1 shows a rolling mill 1, for example, a four-high rolling stand. The rolling mill 1 consists of four rolls 2, namely, two work rolls 2a and two backup rolls 2b supporting the work rolls 2a.

The rolls 2 are rotatably supported in housing posts 3 by means of housing bearings 3a. The rolls 2 can be screwed down by means of hydraulic screw-down cylinders 7, which are, however, kept free of pressure during a test procedure and therefore remain inactive.

A swivel arm 8a (FIG. 2) is supported in the housing post 3 for the upper work roll 2a. It is swiveled upward into a parking position 9 and swiveled downward with its transmission head 10 into the testing position 11. In the testing position 11, the transmission head 10 is pressed firmly against the barrel edge 2f at one end 2c of the roll (FIG. 1) and against the roll surface 2e near the roll neck 2g at the other end 2d of the roll. Means for guiding and cooling the rolling stock are not adversely affected during this procedure and can remain in their operating configuration.

Figure 2:
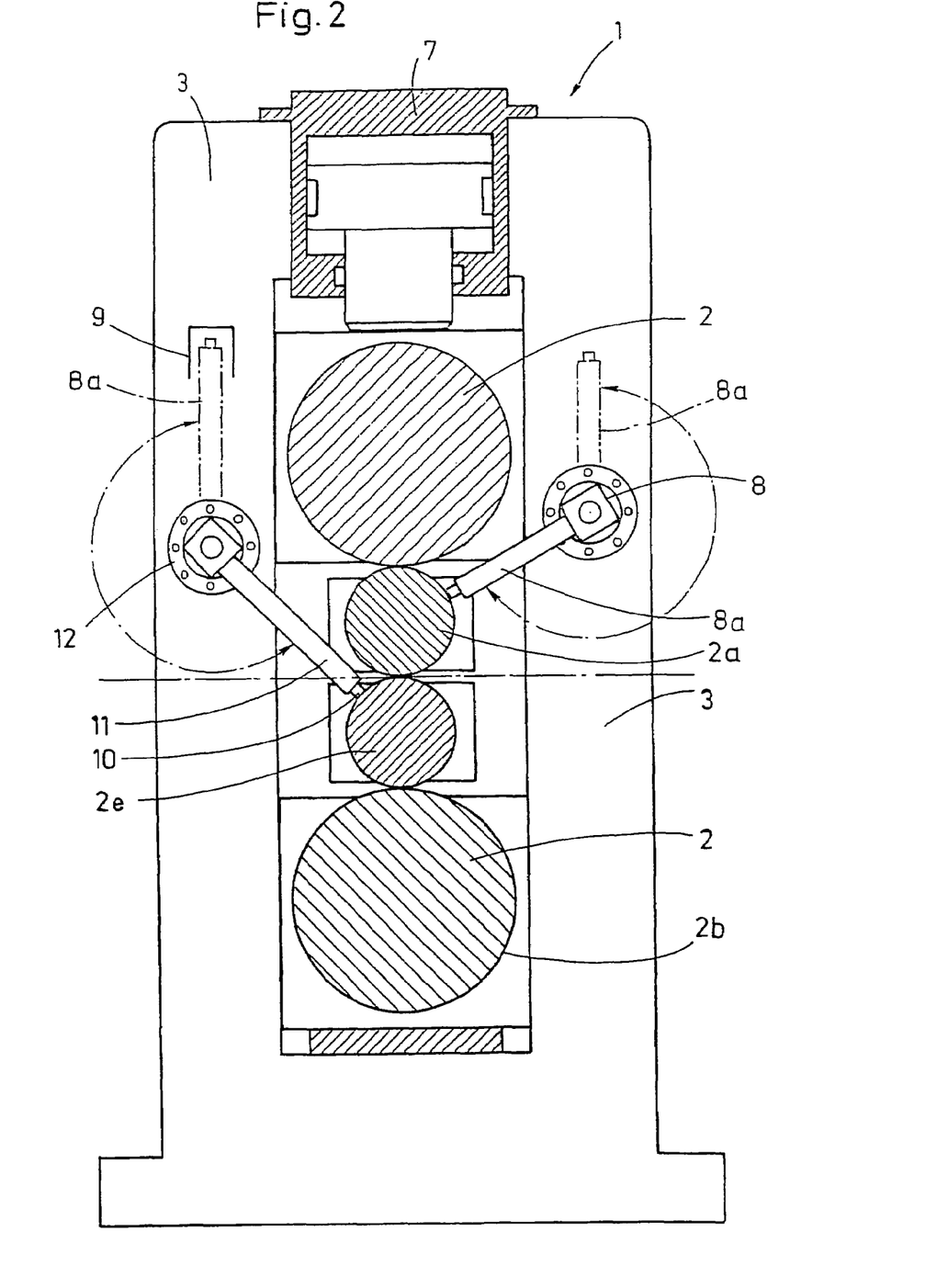
FIG. 2 shows a cross section of FIG. 1 with an ultrasonic transducer and an ultrasonic receiver.

According to FIG. 2, the holders 8 with the transmission heads 10 are easily protected from the adverse surrounding conditions. Two holders 8 each are provided for detecting defects in the upper work roll 2a and the lower work roll 2a.

Figure 3:
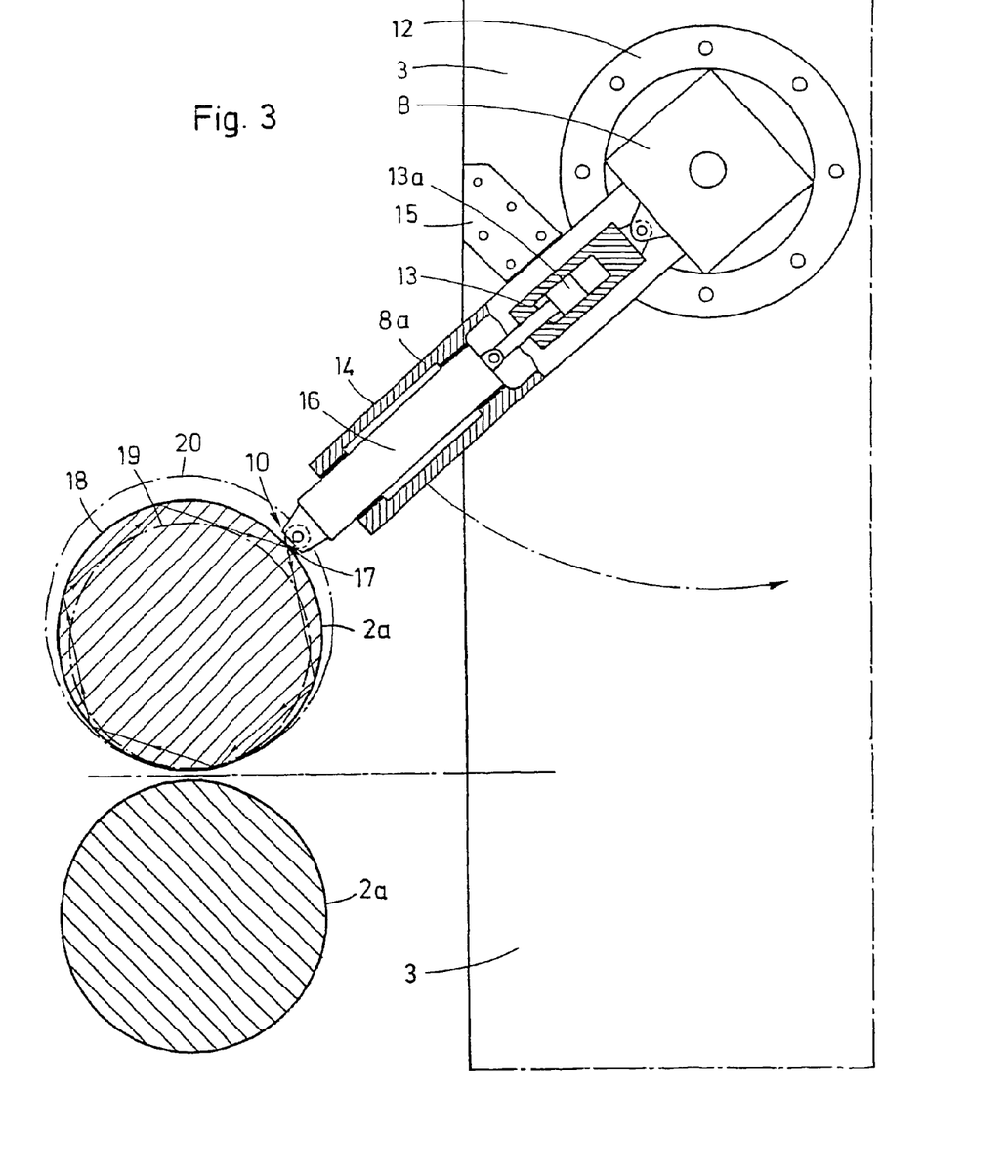
FIG. 3 shows a partial cross section through the holder with contacting means for the ultrasonic transducer or ultrasonic receiver.

FIG. 3 shows an enlarged view of one of the swivel arms 8a, which is supported in a swivel bearing 12 in the housing post 3. The swivel arm 8a is part of the holder 8. A drive 13, e.g., a hydraulic cylinder 13a, is pivoted at both ends inside the holder 8. The housing 14 can be positioned against a stop 15 for fixing the location of a testing position 11, to which the arm is to be repeatedly moved. The hydraulic cylinder 13a is pivoted with a displaceable rod 16 in the housing 14, and the rod 16 carries the transmission head 10 at its tip. The transmission head 10 consists of a contact roller 17. In the illustrated position, the transmission head 10 is in contact with the upper work roll 2a, which has a mean roll diameter 18. The setting direction of the rod 16 is towards the center of the work roll 2a. In the case of changing roll diameters 19, 20, e.g., due to grinding of the roll barrel that has been carried out in the meantime, compensation takes place by the stroke of the hydraulic cylinder 13a. The use of the contact roller 17 (made of steel) results in only negligible displacement of the contact angle. The contact force of the transmission head 10 is controlled by the hydraulic cylinder 13a.

Figure 4:
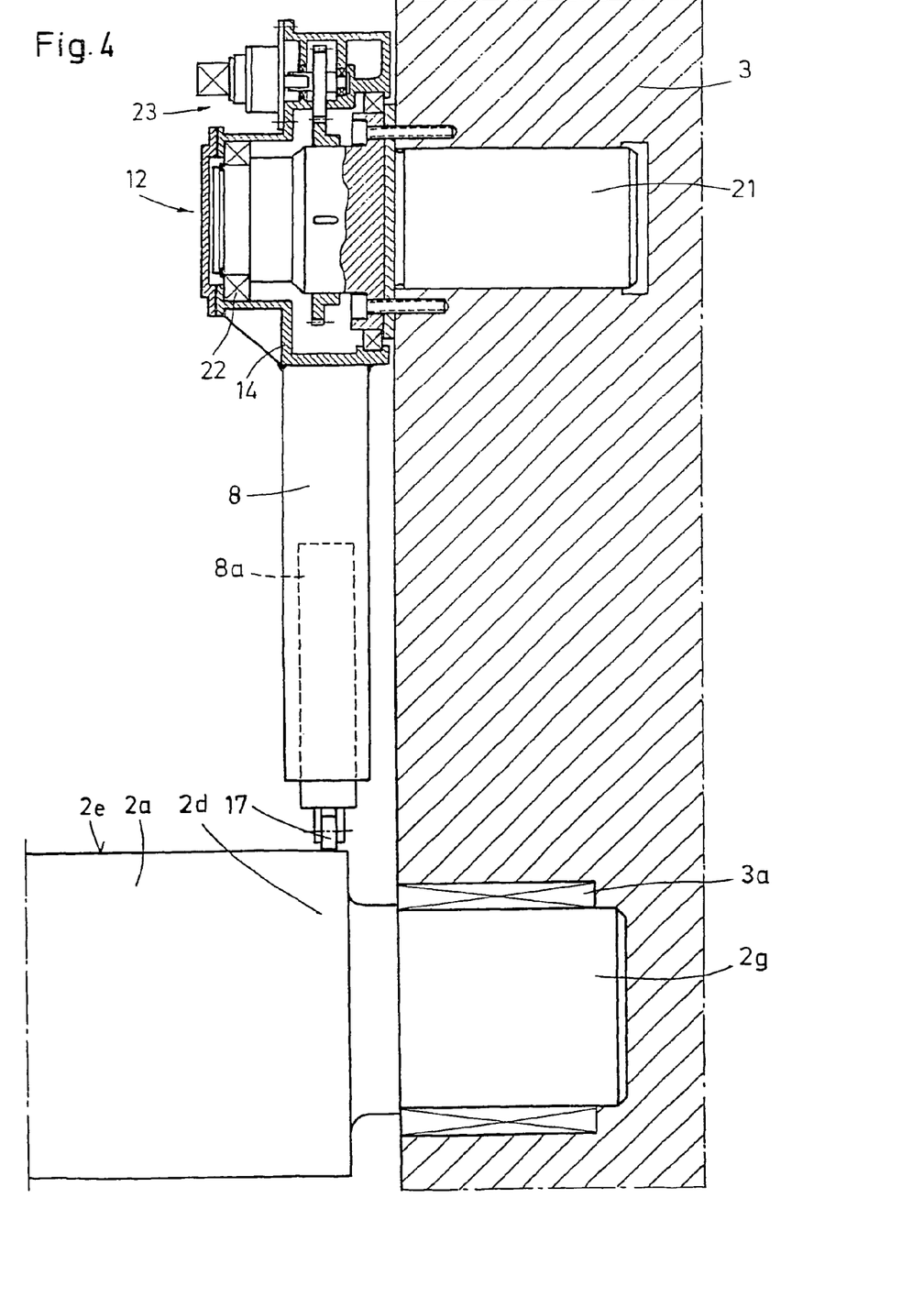
FIG. 4 shows a cross section through the housing post with the holder in its applied position.

FIG. 4 shows a side view of the arrangement of the holder 8 with the swivel arm 8a. The housing 14 holds the swivel bearing 12. The swivel bearing 12 consists of a pivot 21 mounted in the housing post 3. The housing 14 is rotated about the pivot 21 by means of a pivot bearing 22 and a hydraulic pivot drive 23 supported on the housing post 3. This moves the swivel arm 8a out of the parking position 9 and into the testing position 11.

Figure 5:
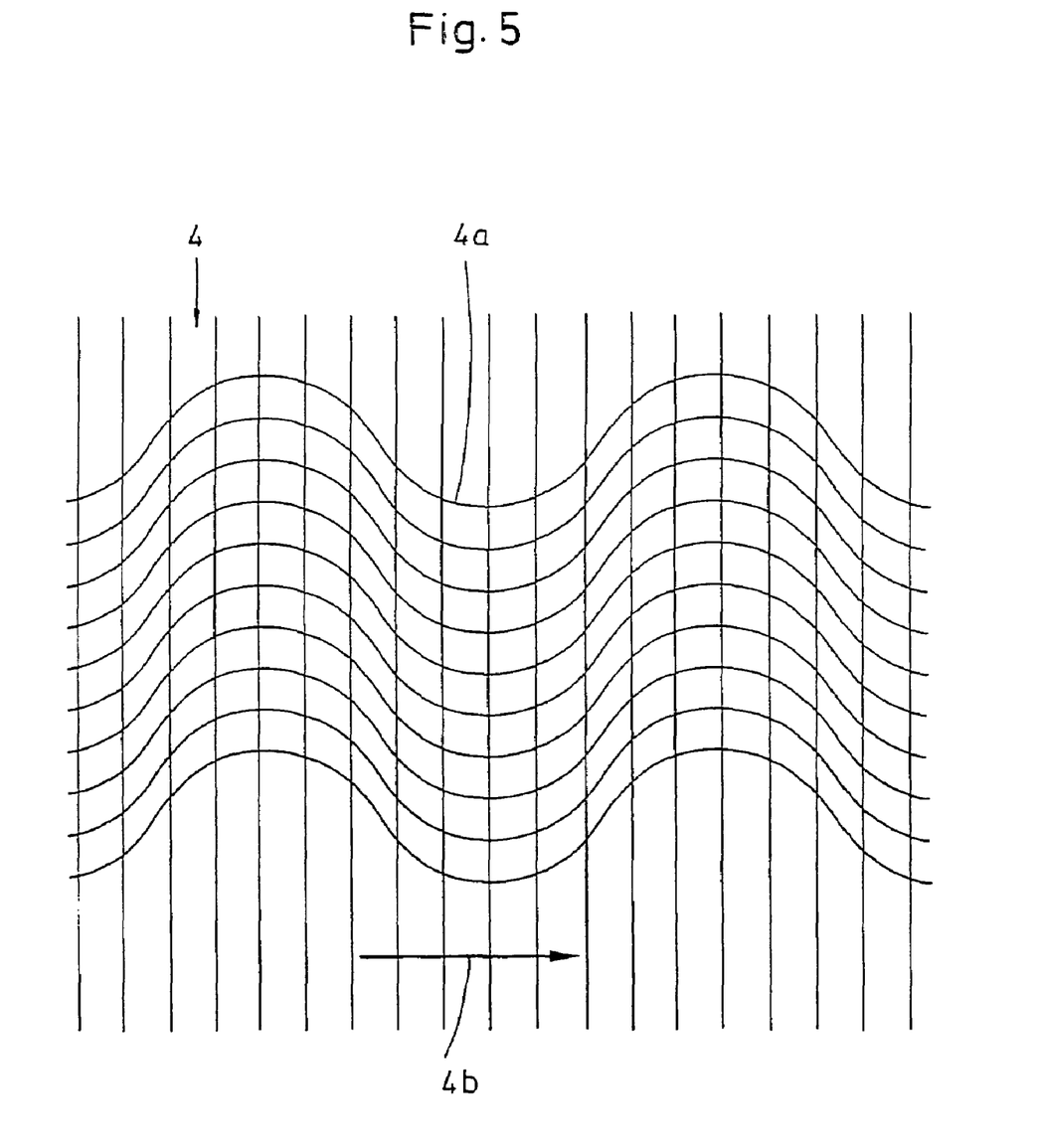
FIG. 5 shows a family of ultrasonic waves.

FIG. 5 shows the ultrasonic waves 4 used for the testing. They are ultrasonic transverse waves 4a which move in direction 4b.

Figure 6:
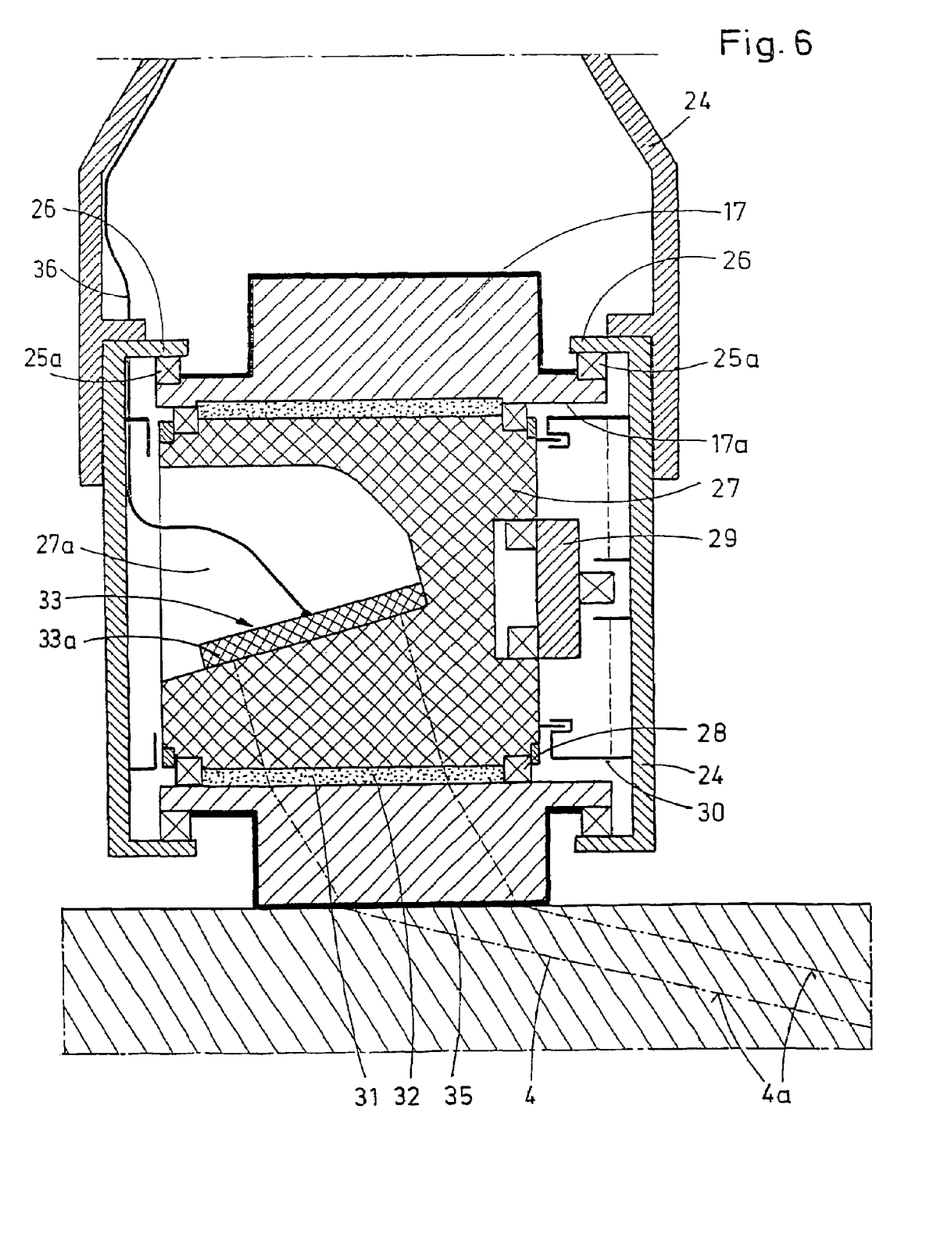
FIG. 6 shows a cross section through a joint of the holder.

As shown in FIG. 6, the contact roller 17 is supported inside a head housing 24, which can be part of the housing 14. The contact roller 17 is rotatably supported by means of roller bearings 25a, 25b. The roller bearings 25a, 25b are sealed against flanges 26 of the head housing 24. A core part 27 made of transparent, glassy plastic (e.g., commercially available plastic glass) is arranged inside the roller bore 17a. The core part 27 is held in a mounting that consists of four sealed bearings 28 and a coupling 29, preferably an Oldham coupling. The plastic core part 27 is insulated and protected by a noncontact seal 30. A filling 32 in the form of an annular layer of silicone for acoustic coupling is introduced into the resulting annular space 31 between the contact roller 17 and the plastic core part 27. A piezoelectric element 33a is mounted inside a cavity 27a as part of the wave transducer 33 (or wave receiver).

Ultrasonic waves 4 generated in an ultrasonic generator 34 (see FIG. 9) are transmitted by the piezoelectric element 33a, through the plastic core part 27 and the filling 32, into the contact roller 17, whose circumference is coated with a layer of iridium 35, and into the roll 2a (made of steel), against which the contact roller 17 is firmly pressed. This results in double refraction of the ultrasonic waves 4.

Figure 8:
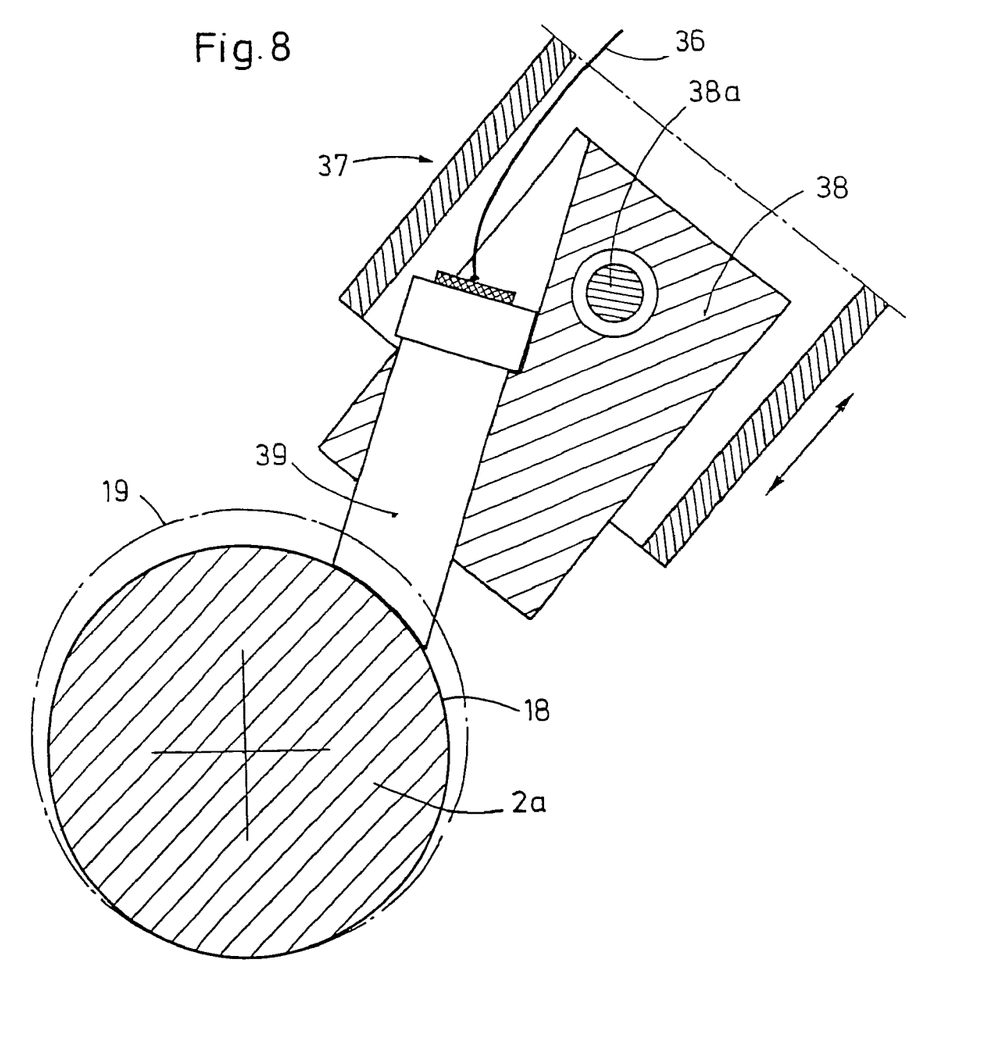
FIG. 8 shows a cross section through another embodiment of the holder.
Figure 9:
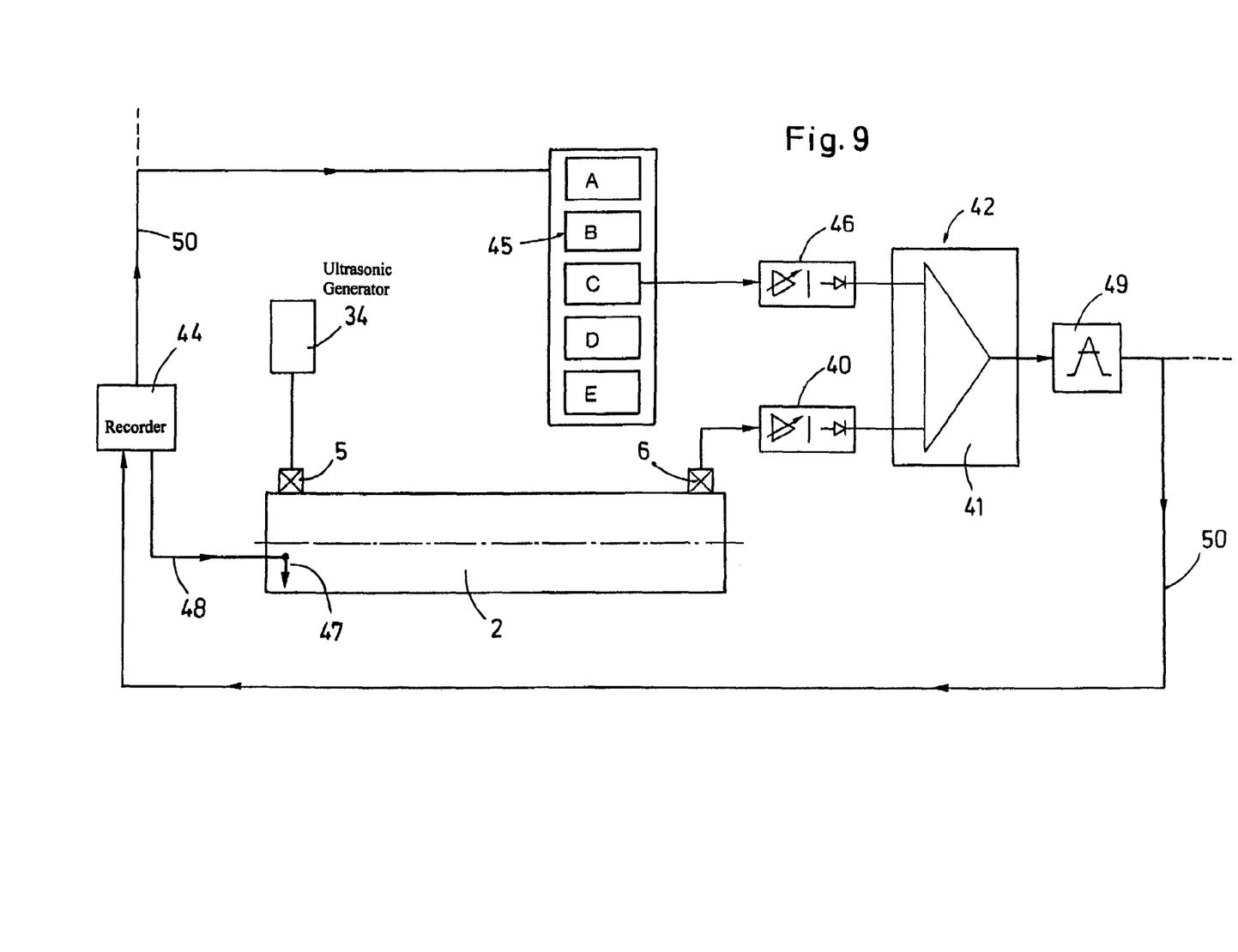
FIG. 9 shows a functional block diagram for the sequence of operations of one or more testing procedures.

The piezoelectric element 33a is connected by a cable 36 with the ultrasonic generator 34 (FIGS. 6, 8, and 9).

The silicone filler 32 is one of various viscous liquids that are suitable as coupling media for ultrasonic waves 4. The ultrasonic waves 4 emerge from the piezoelectric element 33a, pass through the core part 27, which is made of (transparent) plastic, and enter the silicone filling 32. At the exit plane to the steel contact roller 17, the ultrasonic waves 4 are refracted for the first time. The ultrasonic waves 4 then pass through the iridium coating 35 and reach the roll surface 2e as transverse ultrasonic waves 4a. At the roll surface 2e, they are refracted for the second time and enter the steel of the work roll 2a that is to be tested (see FIG. 6, bottom right). A longitudinal component passes through the roll 2 in the longitudinal direction and strikes any surface defects that may be present, such as cracks, checks, spalling, and the like, which are determined as defects.

Figure 7:
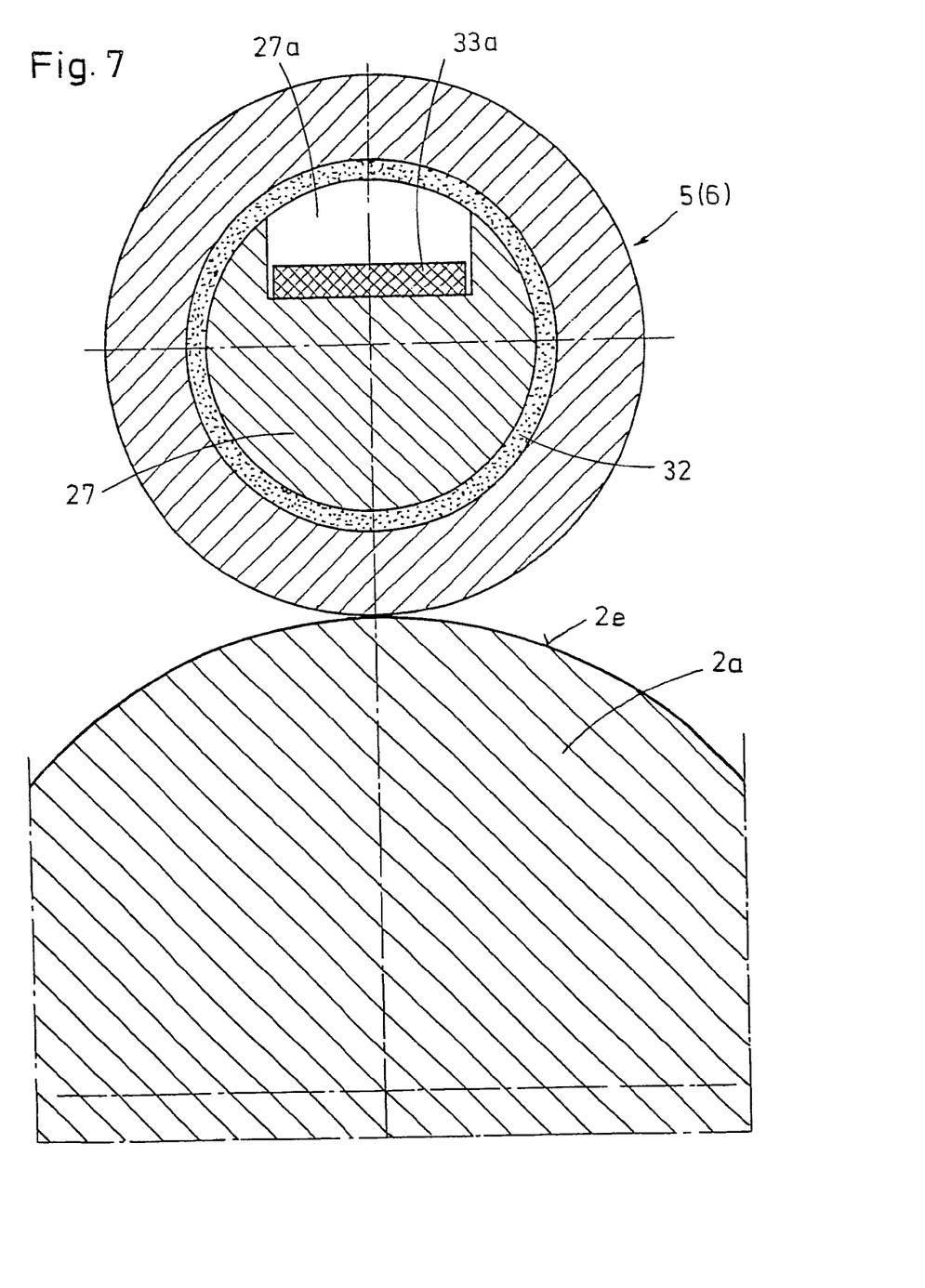
FIG. 7 shows a cross section through a steel roller, which has been placed against a work roll and is mounted on the holder, with part of the transducer.

In FIG. 7, the roller-shaped contact body 17 is supported on a steel work roll 2a. The contact roller 17, which has an iridium coating 35 on its circumference, is pressed firmly against the work roll 2a. This results in double refraction of the ultrasonic waves 4.

The piezoelectric element 33a is connected by a cable 36 with the ultrasonic generator (FIG. 9).

The silicone filler 32 is one of various viscous liquids that are suitable as coupling media for ultrasonic waves 4. The ultrasonic waves 4 emerge from the piezoelectric element 33a, pass through the core part 27, and enter the silicone filling 32.

At the exit plane to the steel contact roller 17, the ultrasonic waves 4 are refracted for the first time. The ultrasonic waves 4 then pass through the iridium coating 35 and reach the roll surface 2e, where they are refracted for the second time.

A longitudinal component passes through the roll 2 in the longitudinal direction and strikes any surface defects that may be present, such as cracks, checks, spalling, and the like, which are determined as the defects that are being sought.

In FIG. 7, the roller-shaped contact body 17 is supported on a steel work roll 2a. The core part 27 (made of transparent plastic) is surrounded by the silicone filling 32 for acoustic coupling. The cavity 27a contains a wave transducer/wave receiver 33, which consists of a piezoelectric element 33a, which is shown in cross section. The ultrasonic transducer 5 (or the ultrasonic receiver 6) sets down momentarily on the roll surface 2e and is then carried along and caused to rotate by the moving roll surface 2e.

FIG. 8 shows an alternative embodiment. The ultrasonic transducer 5 (or the ultrasonic receiver 6, to which the emitted waves are transmitted) is mounted in a swivel head 37, which automatically adjusts itself to the proper angular position. To this end, a carrier 38 can be rotated about a carrier axis 38a, and an oblong contact body 39 is adjusted at a suitable angle to the mean roll diameter 18 and to the changing roll diameter 19. Instead of the silicone filling 32, oil can be introduced as the coupling medium.

It is not necessary to use the testing method and the device in all of the rolling mills of a rolling train. It is sufficient if the rolling mill with the greatest load (with the greatest draft) is tested, since there is a high probability that cracking will first take place there.

FIG. 9 shows a functional block diagram of a device for evaluating signal patterns that have been obtained. The ultrasonic transducer 5 is connected to the ultrasonic generator 34 and, through the roll 2, with the ultrasonic receiver 6, which is connected to a receiver amplifier 40 and a comparator 41. A following memory oscillograph 42 generates an error signal when there is a difference between two signals. The difference comes about by virtue of the fact that the error signal is conducted over a line 43 and a recorder 44, and in a memory 45 for sample measuring signals A, B, C, D, E, etc., a next following reference sample is selected and passed on to an amplifier 46 for samples. If a comparison in the comparator 41 fails to show agreement, a command is issued, e.g., in the event of a difference, to the recorder 44 to reroute to the next sample measuring signal A, B, C, D, E, etc. After completion of the comparisons with the available sample measuring signals, another test is carried out by a rotation 47 about a preset angle 48 (angle ☐). After these procedures, additional comparison operations are initiated in the error signal generator 49 (when there is nonagreement of the signals) and carried out by a relay 50.

LIST OF REFERENCE NUMBERS

1 rolling mill
2 roll
2a work roll
2b backup roll
2c first end of roll
2d second end of roll
2e roll surface
2f barrel edge
2g roll neck
3 housing post
3a housing bearing
4 ultrasonic waves
4a transverse ultrasonic waves
4b direction of propagation
5 ultrasonic transducer
6 ultrasonic receiver
7 screw-down cylinder
8 holder
8a swivel arm
9 parking position
10 transmission head
11 testing position
12 swivel bearing
13 drive
13a hydraulic cylinder
14 housing
15 stop
16 rod
17 contact roller
17a roller bore
18 mean roll diameter
19 changing roll diameter
20 changing roll diameter
21 pivot
22 pivot bearing 23 pivot drive
24 head housing
25a roller bearing
25b roller bearing
26 flange
27 core part made of (transparent) plastic
27a cavity
28 sealed bearing
29 (Oldham) coupling
30 seal
31 annular space
32 silicone filling
33 wave transducer/wave receiver
33a piezoelectric element
34 ultrasonic generator
35 iridium coating
36 cable
37 swivel head
38 carrier
38a carrier axis
39 contact body
40 receiver amplifier
41 comparator
42 memory oscillograph
43 line
44 recorder
45 memory
46 amplifier for samples
47 rotation about angle □
48 preset angle
49 error signal generator
50 relay

The invention claimed is:

1. A method for determining surface defects such as cracks, spalling, on work rolls (2a) of a rolling mill (1) that are supported with backup rolls (2b) in housing posts (3), by the use of ultrasonic waves (4), wherein the roll (2) in which defects are to be detected is tested in its installed position, the method comprising the steps of firmly pressing an ultrasonic transducer (5) and an ultrasonic receiver (6) against the surface (2e) of the roll for the duration of the test, and introducing ultrasonic transverse waves (4a) with a frequency of about 0.5 to 2 MHz at one end (2c) of the roll and receiving the ultrasonic waves at the other end (2d) of the roll, where the ultrasonic waves (4) are conveyed via a piezoelectric element (33a) through a core part (27) of transparent plastic and an adjacent silicone filling (32) to a roller-shaped contact body (17) made of steel, which is pressed against the roll surface (2e) at one end of the roll barrel.

2. A method in accordance with claim 1, wherein the ultrasonic transducer (5) and the ultrasonic receiver (6) are applied radially at the edge (2f) of the barrel, close to the roll neck (2g), which is supported in the housing bearing (3a).

3. A method in accordance with claim 1, wherein, when the ultrasonic transducer (5) and the ultrasonic receiver (6) are being applied, the roll (2) in which defects are to be detected is stopped, and then, after the transducer and receiver have been applied, the roll is turned by about two revolutions.

4. A method in accordance with claim 1, wherein an iridium coating (35) is applied on the outer running surface of the roller-shaped contact body (17).

5. A method in accordance with claim 1, wherein the testing operation is carried out without rolling stock between the work rolls (2a).

6. A method in accordance with claim 1, wherein the ultrasonic waves (4) are introduced into the roll surface (2e) at an acute angle, and only the component in the direction of the roll surface (2e) is utilized.

7. A device for determining surface defects such as cracks, spalling, on work rolls (2a) of a rolling mill (1) that are supported with backup rolls (2b) in housing posts (3), with the use of ultrasonic waves (4), where a holder (8), which can be swiveled out of a parking position (9) and into a testing position (11) or vice versa, is supported in the housing posts (3), and where the holder (8) holds either an ultrasonic transducer (5) or an ultrasonic receiver (6), and where the holder (8) can be adjusted to a definite contact force by means of a drive (13), wherein a roller-shaped contact body (17) made of steel is arranged at the pressing ends of the swivel arms (8a), where the contact roller (17) has a stationary core part (27) made of plastic, and where the annular space (31) between the contact roller (17) and the stationary plastic core part (27) is filled with silicone (32) for acoustic coupling.

8. A device in accordance with claim 7, wherein the stationary core part (27) made of plastic is rotationally rigidly connected with a head housing (24) by a coupling (29), where the core part (27) is supported in the contact roller (17) in such a way that it can rotate smoothly, and where an electrically connected wave transducer (33) or wave receiver (33) is mounted in the contact roller (17).

9. A device in accordance with claim 7, wherein the outer surface of the contact roller (17) is coated with iridium (35).

10. A device in accordance with claim 7, wherein it additionally has a circuit, where an ultrasonic transducer (5) is connected to an ultrasonic generator (34) and, through the roll (2), with an ultrasonic receiver (6), which is connected to a receiver amplifier (40) and a comparator (41), where a memory (45) for sample measuring signals (A, B, C, D, E, etc.) is connected with a parallel amplifier (46) for the samples and with the comparator (41), and where a predetermined sample measuring signal (A, B, C, D, E, etc.) is generated in an error signal generator (49) connected to the comparator (41).

11. A device in accordance with claim 10, wherein the error signal generator (49) is connected to a recorder (44) with memory (45).

12. A device in accordance with claims 10, wherein a relay (50) to a following or preceding sample measuring signal (A, B, C, D, E, etc.) is connected to the recorder (44) for a detected sample measuring signal (A, B, C, D, E, etc.).

* * * * *